(12) United States Patent
Flockerzi et al.

(10) Patent No.: US 6,384,047 B1
(45) Date of Patent: May 7, 2002

(54) BENZONAPHTHYRIDINE

(75) Inventors: Dieter Flockerzi, Allensbach; Armin Hatzelmann, Constance, both of (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/424,841

(22) PCT Filed: May 27, 1998

(86) PCT No.: PCT/EP98/03118

§ 371 Date: Dec. 3, 1999

§ 102(e) Date: Dec. 3, 1999

(87) PCT Pub. No.: WO98/55481

PCT Pub. Date: Dec. 10, 1998

(30) Foreign Application Priority Data

Jun. 3, 1997 (AT) ............................................ 97108892
Jun. 3, 1997 (DE) ......................................... 197 23 161

(51) Int. Cl.⁷ ........................ C07D 471/04; A61K 31/47
(52) U.S. Cl. ........................... 514/292; 546/81; 546/92
(58) Field of Search ........................... 514/292; 546/81, 546/92

(56) References Cited

U.S. PATENT DOCUMENTS 5,346,904 A * 9/1994 Flockerzi et al. ........... 514/292

FOREIGN PATENT DOCUMENTS

| DE | 2 123 328 | 12/1971 |
|---|---|---|
| DE | 43 10 050 | 10/1993 |
| EP | 0 247 971 | 12/1987 |
| EP | 0 163 965 | 12/1996 |
| WO | 91/17991 | 11/1991 |
| WO | 93/09780 | 5/1993 |

* cited by examiner

Primary Examiner—Alan L. Rotman
(74) Attorney, Agent, or Firm—Jacobson Holman, PLLC

(57) ABSTRACT

Compounds 8,9-diethoxy-2-methyl-6-[4(p-toluenesulfonamide) phenyl]-1,2,3,4,4a,10b-hexahydrobenzo[c][1,6]naphthyridine and 9-ethoxy-8-methoxy-2-methyl-6-[4-(p-toluenesulfonamido)phenyl]-1,2,3,4,4a,10b-hexahydrobenzo[c][1,6]naphthyridine and medicament compositions based thereon are useful for treating airway disorders, high blood pressure disorders and concomitant disorders connected therewith.

9 Claims, No Drawings

BENZONAPHTHYRIDINE

RELATED DISCLOSURE

The subject invention is directed to compounds related to those disclosed and claimed in application Ser. No. 09/284,458 (now U.S. Pat. No. 6,008,215), filed Apr. 16, 1999.

FIELD OF APPLICATION OF THE INVENTION

The invention relates to novel benzonaphthyridines, a process for their preparation, their use and medicaments containing them. The compounds according to the invention are used in the pharmaceutical industry for the preparation of medicaments.

KNOWN TECHNICAL BACKGROUND

WO91/17991 describes under the title "New sulphonyl compounds" certain benzonaphthyridine derivatives, which are to be suitable for the treatment of airway disorders. In WO93/09780 and in DE-OS 4310050 the use of these benzonaphthyridine derivatives for the treatment of dermatoses, allergic rhinitis and conjunctivitis as well as of nasal polyps is described. For the compound (−)-cis-8,9-Dimethoxy-2-methyl-6-[4-(p-toluenesulfonamido)-phenyl]-1,2,3,4,4a,10b-hexahydrobenzo[c][1,6]naphthyridine, which is particularly emphasized in WO91/17991, WO93/09780 and DE 4310050, the WHO has proposed the INN Tolafentrine.

DESCRIPTION OF THE INVENTION

The invention relates to compounds of the formula I

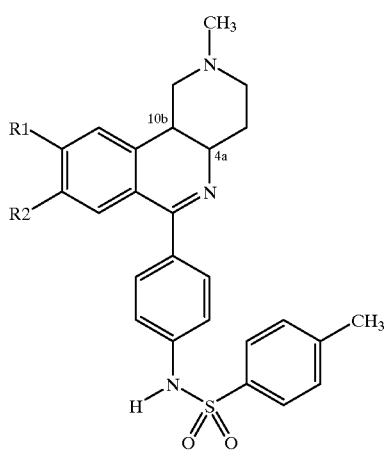

(I)

in which
R1 is ethoxy,
R2 is methoxy or ethoxy,
and the salts of these compounds.

The compounds of the formula I are chiral compounds having chiral centers in positions 4a and 10b. The Invention therefore both comprises all conceivable pure diastereomers and pure enantiomers, and their mixtures in any mixing ratio, including the racemates. Preferred compounds of the formula I are those in which the hydrogen atoms in the positions 4a and 10b are cis to one another.

Particularly preferred are the compounds
(−)-cis-8,9-Diethoxy-2-methyl-6-[4-(p-toluenesulfonamido)-phenyl]-1,2,3,4,4a,10b-hexahydrobenzo-[c][1,6]naphthyridine and
(−)-cis-9-Ethoxy-8-methoxy-2-methyl-6-[4-(p-toluenesulfonamido)-phenyl]-1,2,3,4,4a,10b-hexahydrobenzo[c][1,6]naphthyridine and the salts of these compounds.

Suitable salts for compounds of the formula I preferably are all acid addition salts. Particular mention may be made of the pharmacologically tolerable salts with the inorganic and organic acids customarily used in pharmacy. Examples of such suitable salts are water-soluble and water-insoluble acid addition salts with acids such as for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

The invention further relates to a process for the preparation of the compounds of the formula I, in which R1 and R2 have the meanings indicated above, and their salts.

The process is characterized in that a) compounds of the formula II

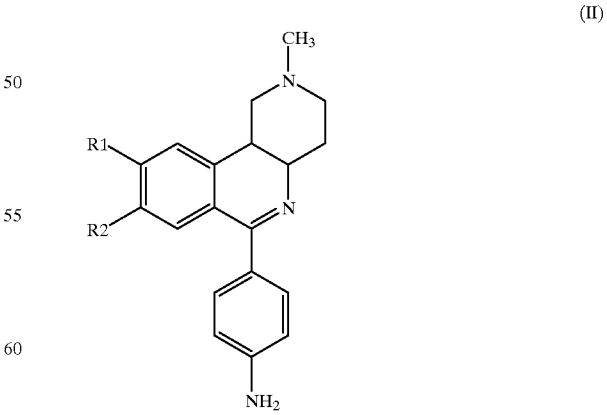

(II)

in which R1 and R2 have the abovementioned meanings, are reacted with a reactive derivative of p-toluenesulfonic acid, or in that b) compounds of the formula III

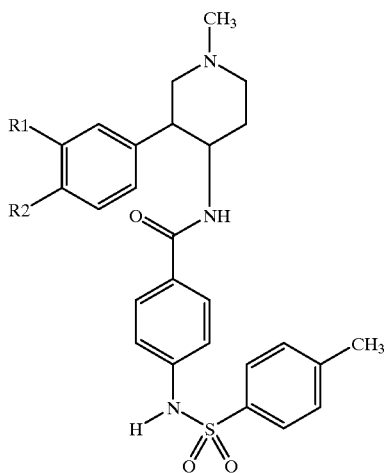

(III)

in which R1 and R2 have the abovementioned meanings, are subjected to a cyclocondensation reaction and in that, If desired, compounds of the formula I obtained according to a) or b) are then converted Into their salts, or in that, if desired, salts of the compounds of the formula I obtained according to a) or b) are then converted into the free compounds.

The reaction of compounds of the formula II with reactive derivatives of the p-toluenesulfonic acid (for example, a p-toluenesulfonic acid halide, particularly the acid chloride) is carried out in inert solvents in a manner known to the expert for the preparation of sulfonamides. The reaction is preferably carried out in the presence of an auxiliary base, such as for example, triethylamine or pyridine.

The cyclocondensation is carried out in a manner known per se to the person skilled in the art according to Bischler-Napieralski (e.g. as described in J. Chem. Soc., 1956, 4280–4282) in the presence of a suitable condensing agent, such as, for example, polyphosphoric acid, phosphorus pentachloride, phosphorus trichloride, phosphorus pentoxide, thionyl chloride or preferably phosphorus oxychloride, in a suitable inert solvent, e.g. in a chlorinated hydrocarbon such as chloroform, or in a cyclic hydrocarbon such as toluene or xylene, or another inert solvent such as acetonitrile, or without a further solvent using an excess of condensing agent, preferably at elevated temperature, in particular at the boiling temperature of the solvent or condensing agent used.

The described methods of preparation can be carried out analogously to the methods described in WO91/17991. The following examples serve to illustrate this.

EXAMPLES 1. (−)-cis-8,9-Diethoxy-2-methyl-6-[4-(p-toluenesulfonamido)-phenyl]-1,2,3,4,4a,10b-hexahydrobenzo[c][1,6]naphthyridine A solution of 2.3 g p-toluenesulfonic acid chloride in 5 ml absolute dichloromethane is added dropwise to a solution of 3.5 g (−)-cis-6-(4-Aminophenyl)-8,9-diethoxy-2-methyl-1,2,3,4,4a,10b-hexahydrobenzo-[c][1,6]naphthyridine in 20 ml absolute pyridine, and the mixture is then stirred at room temperature for a further 3 h. After the evaporation of the solvents, the residue is extracted with dilute sodium hydroxide solution and dichloromethane. The organic phase is then washed with water, dried over sodium sulfate and concentrated. 5.4 g of the title compound are obtained as rough product, which is recrystallised twice in ethyl acetate/methanol. Yield: 4.3 g yellowish crystals. M.p. 267–268° C.

EF: $C_{30}H_{35}N_3O_4S$, MW: 533.70

Optical rotation: $[\alpha]_D^{20}=-88.4°$ (c=1, chloroform/methanol, 1+1) $[\alpha]_{578\ Hg}^{20}=-93.2°$ (c=1, chloroform/methanol, 1+1)

2. (−)-cis-9-Ethoxy-8-methoxy-2-methyl-6-[4-(p-toluenesulfonamido)-phenyl]-1,2,3,4,4a,10b-hexahydrobenzo[c][1,6]naphthyridine 2.52 g (−)-cis-3-(3-Ethoxy-4-methoxyphenyl)-1-methyl-4-[4-(p-toluenesulfonamido)-benzamido]-piperidine are heated to boiling under reflux for 5 h in 4.3 ml phosphorus oxychloride and 60 ml of acetonitrile. After destilling off the excess acetonitrile and phosphorus oxychloride, the residue is partitioned between dichloromethane and saturated sodium hydrogencarbonate solution. The organic phase is washed with water, dried over sodium sulfate and concentrated. After evaporation of the dichloromethane, the residue is purified over silica gel by chromatography. The main product fraction is separated and concentrated. The title compound is obtained after recrystallisation in ethyl acetate/diethyl ether (1:10) as faint yellow fine crystals. M.p. 207–219° C. (unsharp, destruction and red colouring).

EF: $C_{29}H_{33}N_3O_4S \times 0.88H_2O$, MW: 535.49

Optical rotation: $[\alpha]_D^{20}=-65.1°$ (c=1, methanol)

Starting Compounds

A. (−)-cis-3-(3-Ethoxy-4-methoxyphenyl)-1-methyl-4-[4-(p-toluenesulfonamido)-benzamido]-piperidine The title compound is obtained by reaction of 1.36 g (−)-cis-4-Amino-3-(3-ethoxy-4-methoxyphenyl)-1-methylpiperidine with 4-(p-toluenesulfonamido)-benzoyl chloride [prepared from 1.5 g 4-(p-toluenesulfonamido)-benzoic acid and thionyl chloride] in dichloromethane under addition of triethylamine as auxiliary base. 2.65 g are obtained as solid foam. M.p. 100–105° C. (the substance sticks together from about 93° C.).

EF: $C_{29}H_{35}N_3O_5S$, MW: 537.68

Optical rotation: $[\alpha]_D^{20}=-69.6°$ (c=1, methanol)

B. (−)-cis4-Amino-3-(3-ethoxy4-methoxyphenyl)-1-methylpiperidine dihydrochloride The title compound is prepared analogously to the method described in DE 4217401, using rac-3-(3-Ethoxy-4-methoxyphenyl)-1-methylpiperid-4-one instead of rac-3-(3,4-Dimethoxyphenyl)-1-methylpiperid-4-one as starting material.

EF: $C_{15}H_{24}N_2O_2 \times 2HCl \times 0.96H_2O$, MW: 354.52, [colourless crystals (isopropanol)], m.p. 252–254° C.

Optical rotation: $[\alpha]_D^{20}=-65.5°$ (c=1, methanol)

C. (−)cis-4-Amino-3-(3-ethoxy-4-methoxyphenyl)-1-methylpiperidine

The free base is prepared from the dihydrochloride (compound B) by treating with dilute sodium hydroxide solution and extraction with dichloromethane. It is used in the next reaction step without further purification.

COMMERCIAL UTILITY

The compounds according to the invention have valuable pharmacological properties which make them commercially utilizable. As potent inhibitors of type 3, 4 and 5 of cyclic nucleotide phosphodiesterase (PDE3, PDE4 and PDE5), they are suitable on the one hand as bronchial therapeutics (for the treatment of airway obstructions on account of their dilating and cilium-stimulating action but also on account of their respiratory rate- and respiratory drive-increasing action), but on the other hand especially for the treatment of disorders of inflammatory nature, e.g. of the airways (asthma prophylaxis), of the skin, of the intestine, of the eyes and of the joints, which are mediated by mediators such as interferons, members of the tumor necrosis factor family, interleukins, chemokines, colony-stimulating factors, growth factors, lipid mediators (e.g., inter alia, PAF, platelet-activating factor), bacterial factors (e.g. LPS), immunoglobulins, oxygen free radicals and related free radicals (e.g. nitrogen monoxide NO), biogenic amines (e.g. histamine, serotonin), kinins (e.g. bradykinin), neurogenic mediators (such as substance P, neurokinin), proteins such as, for example, granular contents of leukocytes (inter alia cationic proteins of eosinophils) and adherent proteins (e.g. integrins). The compounds according to the invention have smooth muscle-relaxant action, e.g. in the region of the bronchial system, of the blood circulation, and of the efferent urinary passages. Furthermore they have a cilium-frequency increasing action, e.g. in the bronchial system.

In this context, the compounds according to the invention are distinguished by low toxicity, good human acceptance, great therapeutic breadth and the absence of significant side effects.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) airway disorders of various origin (bronchitis, allergic bronchitis, bronchial asthma); disorders with a reduction of the cilium activity or with increased demands on the ciliar clearance (bronchitis, mucoviscidose); dermatoses (especially of proliferative, inflammatory and allergic type) such as, for example, psoriasis (vulgaris), toxic and allergic contact eczema, atopic eczema, seborrheic eczema, lichen simplex, sunburn, pruritis in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on excessive release of TNF and leukotrienes, i.e., for example, disorders of the arthritis type (rheumatoid arthritis, rheumatoid spondylitis, osteoarthritis and other arthritic conditions), systemic lupus erythematosus, disorders of the immune system (AIDS), including AIDS-related encephalopathies, autoimmune disorders such as diabetes mellitus (Type I, autoimmune diabetes), multiple sclerosis and of the type virus-, bacteria- or parasite-induced demyelinization diseases, cerebral malaria or Lyme's disease, shock symptoms [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and of the adjacent regions (paranasal sinuses, eyes), such as, for example, allergic rhinitis/sinusitis, chronic rhinitis/sinusitis, allergic conjunctivitis and also nasal polyps; and also disorders of the central nervous system such as memory disorders and Alzheimer's disease, candidiasis, leishmaniases and leprosy.

On account of their vasorelaxant activity, the compounds according to the invention can also be used for the treatment of high blood pressure disorders of various origin such as, for example, pulmonary high blood pressure and the concomitant symptoms associated therewith, for the treatment of erectile dysfunction or colics of the kidneys and the ureters in connection with kidney stones.

On account of their cAMP-increasing action, however, they can also be used for disorders of the heart which can be treated by PDE inhibitors, such as, for example, cardiac insufficiency, and also as anti-thrombotic, platelet aggregation-inhibiting substances.

The invention further relates to a method for the treatment of mammals including humans who are suffering from one of the abovementioned diseases. The method comprises administering a therapeutically effective and pharmacologically tolerable amount of one or more of the compounds according to the invention to the sick mammal.

The invention further relates to the compounds according to the invention for use in the treatment and/or prophylaxis of diseases, especially the diseases mentioned.

The invention also relates to the use of the compounds according to the invention for the production of medicaments which are employed for the treatment and/or prophylaxis of the diseases mentioned.

The invention furthermore relates to medicaments for the treatment and/or prophylaxis of the diseases mentioned and which contain one or more of the compounds according to the invention.

Advantageously, the substances according to the invention are also suitable for combination with other substances which bring about stimulation of cAMP, such as prostaglandins (PGE2, PGI2 and prostacyclin) and their derivatives, direct adenylate cyclase stimulators such as forskolin and related substances, or substances indirectly stimulating adenylate cyclase, such as catecholamines and adrenergic receptor agonists, in particular beta mimetics. In combination, on account of their cAMP degradation-inhibiting action, they in this case display a synergistic, superadditive activity. This comes to bear, for example, in their use in combination with PGE2 for the treatment of pulmonary hypertension.

The medicaments are prepared by methods known per se familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. Beside solvents, gel-forming agents, ointments bases and other active compound excipients, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, these are administered either directly as a powder (preferably in micronized form) or by atomization of solutions or suspensions which contain them. With respect to the preparations and administration forms, reference is made, for example, to the details in European Patent 163 965.

For the treatment of dermatoses, the compounds according to the Invention are used in particular in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.01 and 10 mg/kg per day.

It is of particular interest for the present invention, that the compounds of formula I according to the invention clearly differ from the structurally closest compound of the state of the art—namely tolafentrine—in a surprising and for the person skilled in the art not foreseeable manner (Data are shown below In the chapter "Biological investigation").

The in-vitro data presented below for the compounds 1 and 2 (the numbers correspond to the numbers of the examples) show promise that the compounds 1 and 2 will have a clearly improved effectiveness in humans in comparison to tolafentrine. The higher potency with regard to the PDE4-inhibition indicates a considerably stronger antiinflammatory capacity, while the more distinct PDE3/PDE5-inhibition indicates a better broncholytic effectiveness.

BIOLOGICAL INVESTIGATIONS

In the investigation of PDE4 inhibition at the cellular level, the activation of inflammatory cells has particular importance. An example which may be mentioned is the FMLP (N-formylmethionylleucylphenylalanine)-induced superoxide production of neutrophilic granulocytes, which can be measured as luminol-potentiated chemiluminescence [McPhail L C, Strum S L, Leone P A and Sozzani S, The neutrophil respiratory burst mechanism. In "Immunology Serie" 1992, 57, 47–76; ed. Coffey R G (Marcel Decker, Inc., New York-Basel-Hong Kong)].

Substances which inhibit chemiluminescence, and/or cytokine secretion, and/or the secretion of inflammation-increasing mediators in inflammatory cells, like T-lymphocytes, monocytes, macrophages and granulocytes are those which inhibit PDE4 or PDE3 and PDE4. The latter isoenzyme of the phosphodiesterase families is particularly represented in granulocytes. Its inhibition leads to an increase in the intracellular cyclic AMP concentration and thus to the inhibition of cellular activation. PDE4 inhibition by the substances according to the invention is thus a central indicator of the suppression of inflammatory processes. (Giembycz MA, Could isoenzyme-selective phosphodiesterase inhibitors render bronchodilatory therapy redundant in the treatment of bronchial asthma? Biochem Pharmacol 1992, 43, 2041–2051; Torphy T J et al., Phosphodiesterase Inhibitors: new opportunities for treatment of asthma. Thorax 1991, 46, 512–523; Schudt C et al., Zardaverine: a cyclic AMP PDE3/4 inhibitor. In "New Drugs for Asthma Therapy", 379–402, Birkhaüser Verlag Basel 1991; Schudt C et al., Influence of selective phosphodiesterase inhibitors on human neutrophil functions and levels of cAMP and Ca; Naunyn-Schmiedebergs Arch Pharmacol 1991, 344, 682–690; Tenor H and Schudt C, Analysis of PDE isoenzyme profiles In cells and tissues by pharmacological methods. In "Phosphodiesterase Inhibitors", 21–40, "The Handbook of Immunopharmacology", Academic Press, 1996; Hatzelmann A et al., Enzymatic and functional aspects of dual-selective PDE3/4-inhibitors. In "Phosphodiesterase Inhibitors", 147–160, "The Handbook of Immunopharmacology", Academic Press, 1996.

A. Methodology
1. Inhibition of the PDE Isoenzymes

The PDE activity was determined according to Thompson et al. (1) with a few modifications (2). The test samples contained 40 mM tris HCl (pH 7.4), 5 mM $MgCl_2$, 0.5 $\mu$M cAMP or cGMP, [$^3$H] cAMP or [$^3$H]cGMP (about 50,000 cpm/sample), the PDE isoenzyme-specific additives described in greater detail below, the given concentrations of inhibitor and an aliquot of the enzyme solution in a total sample volume of 200 kd. Stock solutions of the compounds to be investigated in DMSO were prepared in concentrations such that the DMSO content in the test samples did not exceed 1% by volume—to avoid affecting the PDE activity. After preincubation at 37° C. for 5 minutes, the reaction was started by addition of the substrate (cAMP or cGMP). The samples were incubated at 37° C. for a further 15 min. The reaction was stopped by addition of 50 $\mu$l of 0.2N HCl. After cooling on ice for 10 minutes and addition of 25 $\mu$g of 5'-nucleotidase (snake venom from Crotalus atrox), incubation was carried out again for 10 min. at 37° C. and the samples were then applied to QAE Sephadex A-25 columns. The columns were eluted with 2 ml of 30 mM ammonium formate (pH 6.0). The radioactivity of the eluate was measured and corrected by the corresponding blank values. The proportion of hydrolyzed nucleotide in no case exceeded 20% of the original substrate concentration.

PDE1 ($Ca^{2+}$/calmodulin-dependent) from bovine brain: the inhibition of this isoenzyme was investigated in the presence of $Ca^{2+}$ (1 mM) and calmodulin (100 nM) using cGMP as a substrate (3).

PDE2 (cGMP-stimulated) from rats' hearts was purified chromatographically [Schudt et al. (4)] and investigated in the presence of cGMP (5 $\mu$M) using cAMP as a substrate.

PDE3 (cGMP-inhibited) and PDE5 (cGMP-specific) were investigated in homogenates of human blood platelets [Schudt et al. (4)] using cAMP or cGMP as a substrate.

PDE4 (cAMP-specific) was investigated in the cytosol of human polymorphonuclear leucocytes (PMNL) [isolated from leucocyte concentrates, see Schudt et al. (5)] using cAMP as a substrate. The PDE3 inhibitor motapizone (1 $\mu$M) was used in order to suppress the PDE3 activity emanating from contaminating blood platelets.

2. Inhibition of the Formation of Reactive Oxyyen Species in Human PMNL

The formation of reactive oxygen species determined by means of luminol-potentiated chemiluminescence (5) and the isolation of the PMNL from human blood (6) was carried out essentially as described in (5) and (6): equal-size portions (0.5 ml) of the cell suspension ($10^7$ cells/ml) were preincubated at 37° C. for 5 min. In the absence or presence of the compounds to be investigated in a buffer solution containing 140 mM NaCl, 5 mM KCl, 10 mM HEPES, 1 mM $CaCl_2/MgCl_2$, 1 mg/ml of glucose, 0.05% (w/v) BSA (bovine serum albumin), 10 $\mu$M luminol and 4 $\mu$M microperoxidase. Stock solutions of the compounds to be investigated in DMSO were prepared in such concentrations that the DMSO content—to avoid an effect on the PDE activity—in the test samples did not exceed 0.1% by volume. After preincubation, the test samples were additionally transferred to the measuring apparatus ["Multi-Biolumnat" LB 9505C from Berthold (Wildbad, Germany)] before stimulation with the receptor agonist FMLP (N-formylmethionylleucylphenylalanine, 100 nM). The chemiluminescence was recorded continuously for 3 min.; the AUC values were calculated from this recording.

3. Statistics

The $IC_{50}$ values were determined from the concentration inhibition curves by nonlinear regression using the program GraphPad InPlot™ (GraphPad Software Inc., Philadelphia, USA).

4. References (1) Thompson W. J., Terasaki W. L., Epstein P. M. and Strada S. J., Assay of cyclic nucleotide phosphodiesterase and resolution of multiple molecular forms of the enzyme; Adv. Cycl. Nucl. Res. 1979, 10, 69–92

(2) Bauer A. C. and Schwabe U., An improved assay of cyclic 3',5'-nucleotide phosphodiesterase with QAE Sephadex A-25; Naunyn-Schmiedeberg's Arch. Pharmacol. 1980, 311, 193–198

(3) Gietzen K., Sadorf I. and Bader H., A model for the regulation of the calmodulin-dependent enzymes erythrocyte $Ca^{2+}$-transport ATPase and brain phosphodiesterase by activators and inhibitors; Biochem. J. 1982, 207, 541–548.

(4) Schudt C., Winder S., Müller B. and Ukena D., Zardaverine as a selective inhibitor of phosphodiesterase isoenzymes; Biochem. Pharmacol. 1991, 42, 153–162

(5) Schudt C., Winder S., Forderkunz S., Hatzelmann A. and Ullrich V., Influence of selective phosphodiesterase inhibitors on human neutrophil functions and levels of cAMP and Ca; Naunyn-Schmiedeberg's Arch. Pharmacol. 1991, 344, 682–690

(6) Hatzelmann A. and Ullrich V., Regulation of 5-lipoxygenase activity by the glutathione status in human polymorphonuclearleukocytes; Eur. J. Biochem. 1987, 169, 175–184

B. RESULTS

In Table 1 which follows, the Inhibitory concentrations determined according to Section A1 [inhibitory concentrations as $-\log IC_{50}$ (mol/l)] for the compounds according to the invention are indicated for various PDE isoenzymes. The numbers of the compounds correspond to the numbers of the examples.

TABLE 1

|  | PDE1 | PDE2 | PDE3 | PDE4 | PDE5 |
| --- | --- | --- | --- | --- | --- |
| Tolafentrine | 4.75 | 6.09 | 7.02 | 7.20 | 5.63 |
| 1 | <5 | 5.96 | 7.10 | 8.60 | 7.04 |
| 2 | 5.14 | 6.39 | 7.28 | 9.00 | 6.74 | in table 2 below the inhibitory concentrations determined according to Section A2 for tolafentrine and compound 1 are indicated for the FMLP-stimulated chemiluminiscence in human PMNL.

TABLE 2

| Inhibition of the FMLP-stimulated chemiluminiscence in human PMNL in vitro by tolafentnne and compound 1 [inhibitory concentrations as -log $IC_{50}$ (mol/l)]. | |
| --- | --- |
| Tolafentrine | 6.07 |
| 1 | 7.39 |

What is claimed is:

1. A compound of the formula I

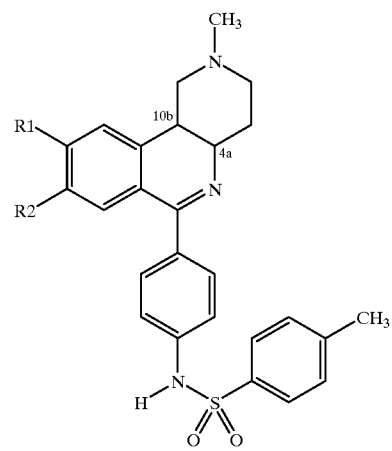

(I)

in which
   R1 is ethoxy,
   R2 is methoxy or ethoxy,
or a salt thereof.

2. A compound of formula I of claim 1 with the chemical name (-)-cis-8,9-Diethoxy-2-methyl-6-[4-(p-toluenesulfonamido)-phenyl]-1,2,3,4,4a,10b-hexahydro-benzo[c][1,6]naphthyridine or a salt thereof.

3. A compound of formula I of claim 1 with the chemical name (-)-cis-9-Ethoxy-8-methoxy-2-methyl-6-[4-(p-toluenesulfonamido)-phenyl]-1,2,3,4,4a,10b-hexahydro-benzo[c][1,6]naphthyridine or a salt thereof.

4. A compound of the formula 1

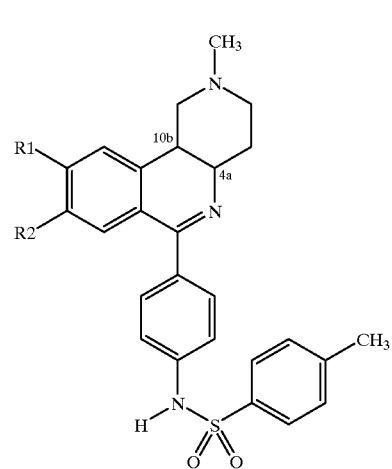

(I)

In which R1 is ethoxy,
   R2 is methoxy or ethoxy,
or a pharmaceutically acceptable salt thereof.

5. A medicament composition comprising an effective amount of a compound as claimed in claim 4 or a pharmaceutically-acceptable salt thereof together with a customary pharmaceutical auxiliary or excipient.

6. A method of treating a subject afflicted with an airway disorder, a high blood pressure disorder or a concomitant disorder connected therewith, which comprises administering to the subject an effective amount of a compound as claimed in claim 4 or of a pharmaceutically-acceptable salt thereof.

7. A method of compounding a medicament composition by combining an active ingredient for treating an airway disorder with a suitable carrier, wherein the active ingredient is a compound as claimed in claim 1 or a pharmaceutically-acceptable salt thereof.

8. A method of producing a medicament composition by combining an active ingredient for treating a high blood pressure disorder or a concomitant disorder connected therewith with a suitable carrier, wherein the active ingredient is a compound as claimed in claim 1 or a pharmaceutically-acceptable salt thereof.

9. A method for treating a condition amenable to treatment with an active ingredient possessing PDE-inhibiting properties, which comprises administering an effective amount of a compound as claimed in claim 1 or a pharmaceutically-acceptable salt thereof to a subject afflicted with the condition.

\* \* \* \* \*